(12) United States Patent
Hoganson

(10) Patent No.: US 11,160,956 B1
(45) Date of Patent: Nov. 2, 2021

(54) BALLOON DILATOR

(71) Applicant: David M. Hoganson, Brookline, MA (US)

(72) Inventor: David M. Hoganson, Brookline, MA (US)

(*) Notice: Subject to any disclaimer, the term of this patent is extended or adjusted under 35 U.S.C. 154(b) by 287 days.

(21) Appl. No.: 15/017,627

(22) Filed: Feb. 6, 2016

Related U.S. Application Data

(60) Provisional application No. 62/113,243, filed on Feb. 6, 2015.

(51) Int. Cl.
*A61M 25/10* (2013.01)
*A61M 25/09* (2006.01)
(Continued)

(52) U.S. Cl.
CPC .......... *A61M 25/10* (2013.01); *A61B 17/3439* (2013.01); *A61B 17/3494* (2013.01);
(Continued)

(58) Field of Classification Search
CPC .............. A61M 25/10; A61M 25/1018; A61M 25/10182; A61M 2025/1068;
(Continued)

(56) References Cited

U.S. PATENT DOCUMENTS 2,828,744 A * 4/1958 Hirsch .................. A61M 5/329
604/165.01
4,404,971 A * 9/1983 LeVeen .............. A61B 17/1204
604/101.05

(Continued)

*Primary Examiner* — Brandy S Lee
*Assistant Examiner* — Hong-Van N Trinh
(74) *Attorney, Agent, or Firm* — Ramberg IP, LLC; Jeffrey R. Ramberg

(57) ABSTRACT

A dilator system for arterial and venous cannulas, where there is a smooth transition between the dilator and the outer wall of the cannula. One aspect of the subject technology provides a blunt-tip cannula that is used as a dilator for insertion of an arterial or venous cannula. The balloon might either be a single diameter or may have a larger diameter at the distal portion such that the diameter of the distal portion of the balloon dilator matches the diameter of the cannula at the tip. Another aspect of the subject technology is a balloon dilator for cannulae that may be positioned over a guidewire, for guidewire-directed placement of a cannula within a vessel, duct, lumen or heart structure of the body. Another aspect of the subject technology is an inflation system for the balloon dilator, such that the balloon dilator may be deflated and quickly removed from the cannula after the cannula has been positioned and secured within the vessel, duct, lumen or heart structure. Another aspect of the subject technology includes a stiffening element in the balloon dilator along its shaft to increase the rigidity of the combined balloon dilator and cannula to provide improved ease of insertion. Another aspect of the subject technology is an improved curvature of the shape of the right angle dilator that achieves more uniform flow within the dilator and ease of insertion and more even flow within the cannula, and ease of insertion of and retraction of the balloon dilator. Another aspect of the subject technology is a gel-filled balloon dilator that improves ease of insertion of the cannula within the vessel, duct, lumen or heart structure, and can be removed without deflation.

28 Claims, 14 Drawing Sheets

(51) Int. Cl.
*A61M 1/36* (2006.01)
*A61B 17/34* (2006.01)

(52) U.S. Cl.
CPC .......... *A61M 1/3659* (2014.02); *A61M 25/09* (2013.01); *A61M 25/1025* (2013.01); *A61M 25/10182* (2013.11)

(58) Field of Classification Search
CPC ...... A61M 25/1025; A61M 2025/0039; A61M 25/1002; A61M 25/1006; A61M 25/1011; A61M 25/1034; A61M 25/1036; A61M 2025/1013; A61M 25/1015; A61M 5/158; A61M 2005/1581; A61M 5/32; A61M 5/3286; A61M 25/065; A61M 25/06; A61M 5/329; A61M 2005/3284; A61M 39/10; A61M 2025/0063; A61M 25/005; A61M 25/0054; A61M 25/0053; A61M 1/3659; A61M 25/09; A61B 17/3439; A61B 17/3494
USPC ................................ 604/524, 525, 526, 527
See application file for complete search history.

(56) References Cited

U.S. PATENT DOCUMENTS

| | | | | |
|---|---|---|---|---|
| 4,808,165 A | * | 2/1989 | Carr | A61M 25/1018 604/97.02 |
| 5,385,562 A | * | 1/1995 | Adams | A61M 25/01 604/159 |
| 5,425,724 A | * | 6/1995 | Akins | A61M 25/06 600/585 |
| 5,456,694 A | * | 10/1995 | Marin | A61F 2/958 623/1.11 |
| 5,549,554 A | * | 8/1996 | Miraki | A61M 25/00 604/101.05 |
| 5,863,366 A | * | 1/1999 | Snow | A61B 17/12022 156/143 |
| 5,868,778 A | * | 2/1999 | Gershony | A61M 25/06 604/96.01 |
| 6,042,576 A | * | 3/2000 | DeVries | A61M 25/007 604/264 |
| 8,747,389 B2 | * | 6/2014 | Goldfarb | A61M 25/10 604/891.1 |
| 2006/0265041 A1 | * | 11/2006 | Sanati | A61F 2/90 623/1.11 |

* cited by examiner

BALLOON DILATOR

CROSS-REFERENCE TO RELATED APPLICATION(S)

This patent document claims the benefit of U.S. Provisional Application No. 62/113,243, filed on Feb. 6, 2015 in the name of David M. Hoganson. The entire contents of this commonly owned patent application are expressly incorporated by reference herein.

STATEMENT REGARDING FEDERALLY SPONSORED RESEARCH

None.

BACKGROUND OF THE INVENTION

Heart surgery and extracorporeal membrane oxygenation (ECMO) are made possible by connecting a patient to a mechanical circulatory support system. The cardiopulmonary bypass circuit, or ECMO circuit, consists of a pump and an oxygenator, which provide the function of the heart and the lungs to support patients during surgery or temporarily during critical illness. Connecting patients to these mechanical circulatory support systems involves placement of cannulas in arterial and venous systems (or just in the venous system) of the patient to drain blood from the patient to the support circuit, and then return that blood to the patient. During heart surgery in particular, cannulas are generally placed in the right atrium or superior vena cava and inferior vena cava to drain blood to the cardiopulmonary bypass machine, and then, in the aorta, to return the blood to the patient.

The cannulas are placed in the venous and arterial system while those vessels are fully pressurized. This includes a well-established technique of placing purse string sutures in a linear, circular or other geometric shape, passing the sutures through a tourniquet and then placing the cannulas within the middle of these purse-string sutures. The cannulas are secured to the tourniquet. The limitation of this system is that many of the cannulas, especially those used for the venous system, are simply cut tubes that are forced into the blood vessels through an open incision and to a pressurized vessel. This is often done with some difficulty, including multiple attempts and significant blood loss. The vessel is held open with significant blood coming out of the incision while the cannula is attempted to be inserted. On occasion, difficulty with cannulation during heart surgery or initiation of ECMO support results in hemodynamic instability of the patient, or even injury to the vessels being cannulated. Many of the straight cannulas, particularly the arterial cannulas, do have a dilator that extends through the lumina of the cannula and projects past the tip of the cannula to ease cannula insertion. However, these dilators are often not well-secured to the cannulas, and can push back into the cannula during insertion and, importantly, there is still a step transition between the greatest diameter of the dilator and the greatest diameter of the cannula, which still can make these cannulas difficult to insert into the patient, particularly a small child with rather elastic vessels.

One particular cannula design that is most difficult to insert is the right angle-style cannulas used generally for superior vena cava and inferior vena cava cannulation, and occasionally for right atrial cannulation. These cannulas generally have an open tube, cut at a 45-degree angle, that can vary from 10 French up to 28 French or larger in diameter. These cannulas have no dilators and can be difficult to easily position into a vein, either deep within the chest of a large patient or in the small and delicate veins of a young child. There is a need in the art for dilator technology for the insertion of arterial and venous cannulas that provide a smooth transition into the blood vessel between the dilator and the cannula for safe, reliable, and improved ease of insertion.

SUMMARY OF THE INVENTION

It is an object of the subject technology to provide a dilator system for arterial and venous cannulas, where there is a smooth transition between the dilator and the outer wall of the cannula.

One aspect of the subject technology provides a blunt-tip cannula that is used as a dilator for insertion of an arterial or venous cannula. The balloon might either be a single diameter or may have a larger diameter at the distal portion such that the diameter of the distal portion of the balloon dilator matches the diameter of the cannula at the tip. The smaller portion of the balloon dilator may then reside within the tip of the cannula. The distal taper of the balloon dilator provides a smooth transition between the tip of the dilator and its maximum diameter.

Another aspect of the subject technology is a balloon dilator for cannulae that may be positioned over a guidewire, for guidewire-directed placement of a cannula within a vessel, duct, lumen or heart structure of the body.

Another aspect of the subject technology is an inflation system for the balloon dilator, such that the balloon dilator may be deflated and quickly removed from the cannula after the cannula has been positioned and secured within the vessel, duct, lumen or heart structure.

The subject technology also provides a means of securing the balloon dilator within the cannula, including a proximal balloon that is simultaneously inflated to secure the position of the dilator within the cannula during insertion and deflated simultaneously with the distal balloon dilator for ease of removal of the dilator system from within the cannula.

Another aspect of the subject technology includes a stiffening element in the balloon dilator along its shaft to increase the rigidity of the combined balloon dilator and cannula to provide improved ease of insertion.

Another aspect of the subject technology is an improved curvature of the shape of the right angle dilator that achieves more uniform flow within the dilator and ease of insertion and more even flow within the cannula, and ease of insertion of and retraction of the balloon dilator.

Another aspect of the subject technology is a gel-filled balloon dilator that improves ease of insertion of the cannula within the vessel, duct, lumen or heart structure, and can be removed without deflation.

It should be appreciated that the present invention can be implemented and utilized in numerous ways, including without limitation as a process, an apparatus, system, device, a kit (e.g., a kit comprising one of the platforms described herein in this first-of-use), and a method for applications now known and later developed. These and other unique features of the system disclosed herein will become more readily apparent from the following description and the accompanying drawings.

BRIEF DESCRIPTION OF THE DRAWINGS

Other aspects and many of the intended advantages of this invention will be readily appreciated, as the same becomes better understood by reference to the following detailed description, when considered in connection with the accompanying drawings wherein.

DETAILED DESCRIPTION OF EMBODIMENTS OF THE INVENTION

Figures 1A, 1B:
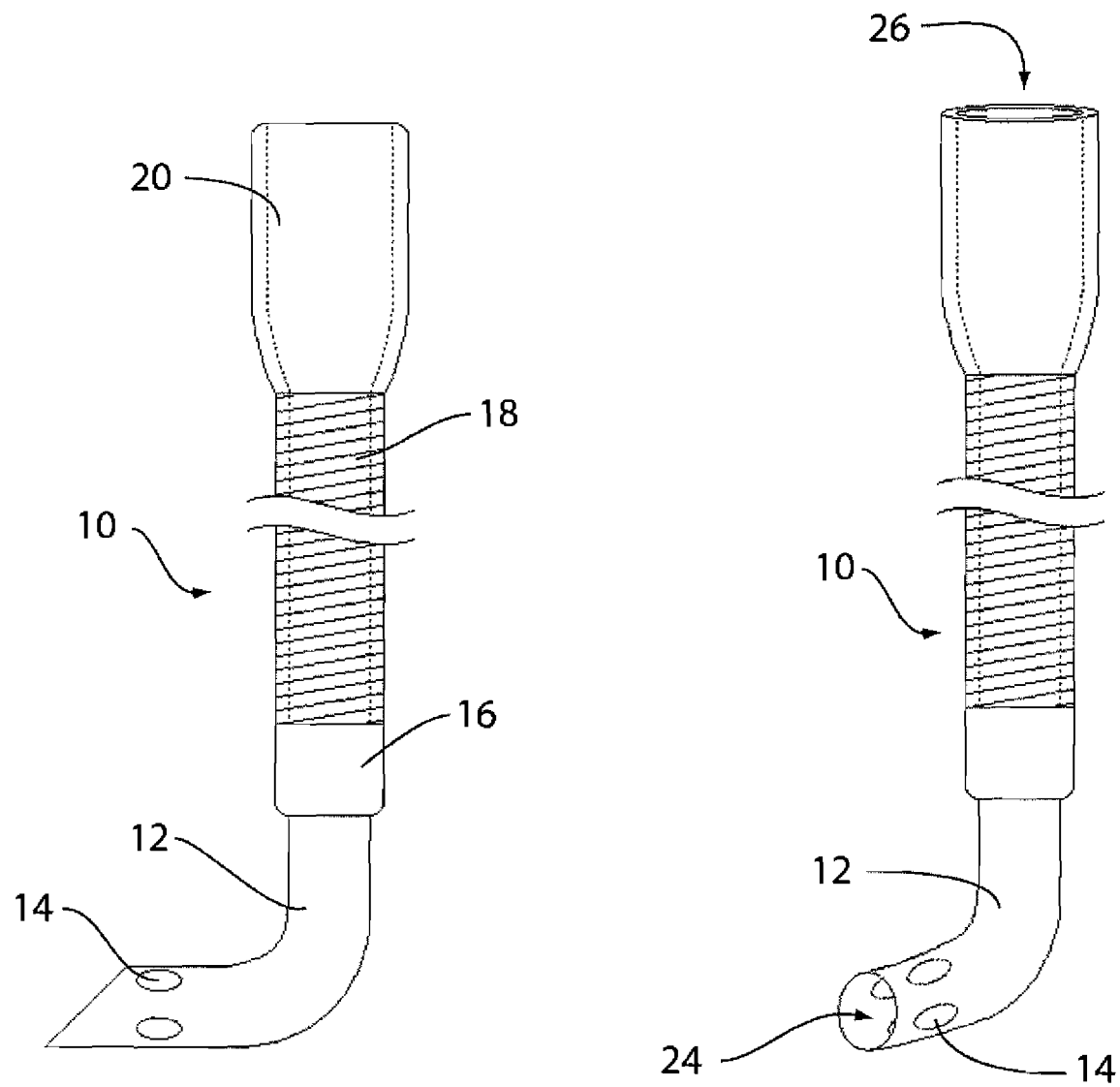
FIG. 1A illustrates a lateral view of a right angle venous cannula.
FIG. 1B illustrates a perspective view of a right angle venous cannula.

The present invention overcomes many of the prior art challenges associated with dilators for arterial and venous cannulas. The advantages and other features of the technology disclosed herein will become more readily apparent to those having ordinarily skill in the art, and the following detailed description of certain embodiments taken into conjunction with the drawing which set forth representative embodiments of the present invention and wherein like reference numerals identify similar structural elements.

It is to be understood that the subject technology is not intended to be limited to the particular constructs and methods described in the described embodiments, as one skilled in the art can extend the concepts involved using variations which are obvious after reading the present disclosure. Although any methods and materials, similar or equivalent to those described herein, may be useful in a practice of the subject technology, certain compositions, films, methods, and materials are described below. All relative descriptions herein, such as "top," "bottom," "left," "right," "up," and "down" are with reference to the figures, and not meant to be in a limiting sense.

Referring to FIG. 1A, a typical right angle venous cannula (10) is shown. The metal or plastic tip (12) is at the distal portion of the cannula with one or more holes (14) in the side of the distal tip (12). There is a connecting element (16) that joins the distal tip to a wire-wound plastic tube (18), which typically extends for approximately 12 inches, which attaches to a flared proximal portion (20). Referring to FIG. 1B is an asymmetric projection view of right angle venous cannula (10), with distal tip (12), side holes (14), and inlet to the cannula. The blood flows into the cannula from a venous or otherwise structure of the body through inlet hole (24), and through the cannula out the exit hole (26) at the proximal end of the cannula. This is a typical design for a right angle venous cannula to be inserted into a vein, atria, or other similar structure. It is intended that the said technology of this invention be applicable to this type of a cannula and past, current, and future variations of this similar design that may be adaptable to any vessel, duct, lumen or heart structure, including but not limited to the trachea, the bowel, the bile duct, urinary structure including the bladder, ureter, or urethras.

Figure 2A:
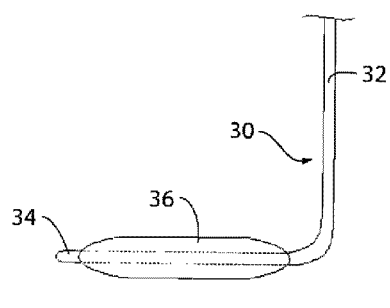
FIG. 2A illustrates a lateral view of a distal portion of a balloon dilator.
Figure 2B:
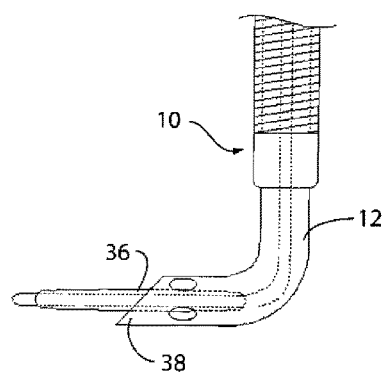
FIG. 2B illustrates a lateral view of a balloon dilator in the deflated position within a right angle venous cannula.
Figure 2C:
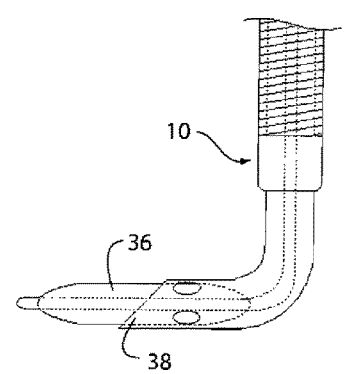
FIG. 2C illustrates a lateral view of a balloon dilator within a right angle venous cannula when the balloon is in the inflated position.

Referring to FIG. 2A, a lateral view of the distal portion of a balloon dilator (30), which includes shaft (32), distal tip (34), and balloon (36). The shaft (32) includes at least one lumen. At least one lumen carries fluid that communicates with the inside of balloon (36). This fluid can be used to inflate and deflate the balloon (36). The fluid to inflate the syringe may be but not limited to a gas such as air or oxygen, a liquid such as water or saline or may be a gel. The distal tip (34) is intended to be an atraumatic tip for entry into a vessel, duct, lumen or heart structure. As shown in FIG. 2B is a typical right angle venous cannula (10) with distal metal or plastic tip (12) wherein the balloon dilator is positioned within the cannula tip, such that the balloon (36) extends in part past the tip (38) of the cannula and, in part, resides within the cannula distal portion (12). As shown here, the balloon is in the deflated position, which may be used for positioning the balloon dilator within the distal portion of the cannula. FIG. 2C shows the venous cannula (12) with the balloon (36) of the balloon dilator inflated, such that the balloon accompanies the entire internal diameter of the distal tip of the cannula and extends past the distal edge of the cannula tip (38). In this embodiment of the design, the outer diameter of the balloon may be smaller than, equal to, or slightly larger than the internal diameter of the distal tip of the cannula. The distance that the balloon extends past the distal tip of the cannula may be variable, depending upon the size of the cannula—in particular, the diameter of the distal tip of the cannula—and the intended use of the cannula. For example, if it is a small right angle venous cannula, such as a 12 French metal tip cannula intended to be used for a cannulation of the superior vena cava of an infant for use in heart surgery, the distance the balloon tip dilator extends past the tip of the venous cannula may be relatively short such that the distance it extends may be on the order of two times the diameter of the cannula with a transition angle between the tip of the dilator and its maximal portion at the balloon's widest portion. And other applications, for example, a large venous cannula, such as a 24 French intended to cannulate the inferior vena cava of an adult, may have a longer portion of the balloon that extends past the tip of the dilator to facilitate ease of entry of the tip into the opening in the inferior vena cava or proximal right atrium. In some applications, the distance the balloon extends past the tip of the cannula may be two or more times the diameter of the cannula.

Figure 3:
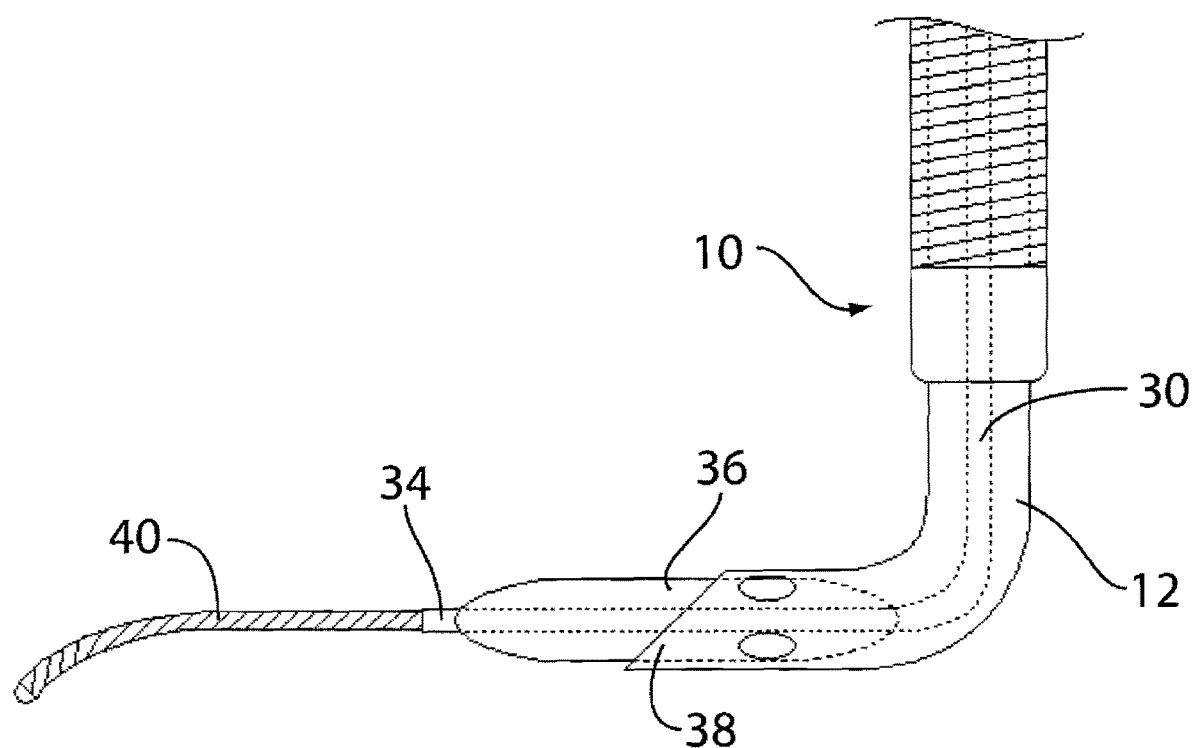
FIG. 3 illustrates a lateral view of a balloon dilator positioned over a guidewire where the balloon is in an inflated position within a right angle venous cannula.

Now referring to FIG. 3, a lateral perspective view of a right angle cannula (10) with distal portion (12) and distal tip (38) and a balloon dilator (33) positioned within the venous cannula, which includes the balloon (36), a distal tip (34), and extending from the lumen of the distal tip (34) is a guidewire (40). In this embodiment, a guidewire may be used initially to access a vessel, duct, lumen or heart structure that is intended to be cannulated. The proximal end of the guidewire (40) may then be threaded through the distal tip (34) of the balloon dilator (33) with the balloon dilator positioned within the venous cannula and already inflated. The balloon dilator and venous cannula construct can then be fed over the dilator and into the target vessel, duct, lumen or heart structure. The guidewire (40) may then be withdrawn, the balloon (36) deflated, and the balloon dilator (33) removed from the venous cannula (10). In this sequence, the right angle venous dilator is positioned within a vessel, duct, lumen or heart structure using traditional guidewire or Seldinger or access. In another embodiment, the guidewire may extend from the balloon dilator and cannula assembly and be inserted through peel-away needle that accesses the intended vessel, duct, lumen or heart structure. The guidewire may be advanced into the vessel, the needle withdrawn and peeled off the guidewire and then the balloon dilator and cannula tip advanced into the vessel, duct, lumen or heart structure. The guidewire access may be used for any shaped cannula with the balloon dilator including but not limited to a straight cannula.

This methodology may be used to safely access a target vessel, duct, lumen or heart structure, especially in an application where the tolerance for blood loss is very low and the intended opening made by the venous cannula very small, as to not damage or significantly reduce the size of the target vessel upon repair after the cannula is removed. Additionally, the guidewire approach may be used in a minimally invasive approach where there is limited access to the structure for cannulation. This may include cannulation of the superior vena cave during a lower mini sternotomy incision or the distal aorta when there is a goal to direct it down the lumen of the descending aorta as two examples. The use of the guidewire may afford the surgeon additional control and accuracy when placing the cannula. The distal tip (34) may have elements on it to facilitate entry into an undilated vessel, duct, lumen or heart structure, such as a superior vena cava. These elements may include blade- or razor-like features which may facilitate small initial incision in the vessel as the balloon dilator begins its entry into the vessel to create a directed initial incision that might then be further opened by the dilating force of the balloon (36) entering the vessel. In another embodiment, the tip (34) of the balloon dilator may have a very tight approximation to the guidewire at its distal portion, and then have a taper or flare as it approaches the balloon to ensure a very smooth transition between the tip and the tapering portion of the balloon (36).

Figure 4A:
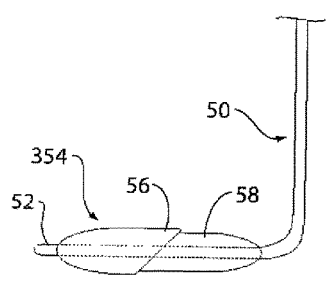
FIG. 4A is a lateral view of a multidiameter balloon dilator.
Figure 4B:
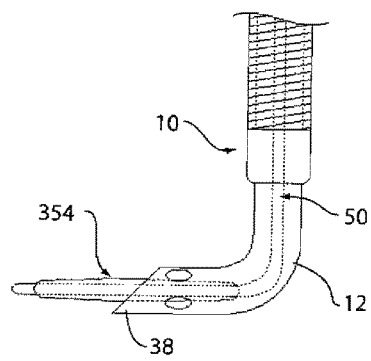
FIG. 4B is a lateral view of a multidiameter balloon dilator in the inflated position within a right angle venous cannula.
Figure 4C:
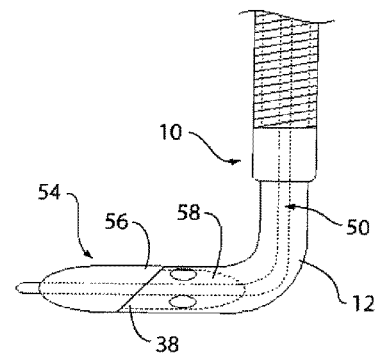
FIG. 4C is a multidiameter balloon dilator in the inflated position within a right angle venous cannula.

Referring to FIG. 4A, what is shown is a lateral perspective view of balloon dilator (50) with tip (52) and multidiameter dilator balloon (354) that includes distal portion (56) featuring a larger diameter, and proximal portion (58) having a smaller diameter. The larger diameter distal portion (56) is intended to have a diameter that is slightly smaller than, equal to, or slightly larger than the largest outer diameter of the distal portion of a cannula or tube intended to enter a vessel, duct, lumen or heart structure. The distal portion (56) of the balloon provides a smooth transition between the tip of the dilator and the cannula, while the proximal portion (58) of the balloon is intended to reside within the distal portion of the cannula, tube, or cylinder and secure the balloon dilator in place. In another embodiment, the distal portion (56) of the balloon has a diameter that is substantially equal to the outer diameter of the distal portion of the right angle cannula (10). Depending upon the shape of the distal portion of the cannula, the transition between the distal portion (56) and the proximal portion (58) of the dilator balloon (354) may be linear directly across the balloon, may be angled, or may have another design to best match the design of the distal tip of the cannula, including but not limited to a curve, multiple steps, multiple angles, and may include more than two diameters of the balloon. FIG. 4B illustrates the balloon dilator (50), with multidiameter balloon (354) positioned within a right angle venous cannula (10) with distal portion (12) and distal tip (38). The balloon (354) is in the deflated position, as it would be with the balloon dilator initially positioned within the cannula or just prior to withdrawal of the balloon dilator. FIG. 4C illustrates the balloon dilator balloon (54) with distal portion (56) and proximal portion (58) in the expanded position within the venous cannula (10). The proximal portion (58) of the balloon nearly or exactly matches the internal diameter of the distal portion (12) of the cannula, whereas after the distal tip (38) of the cannula, the diameter of the distal portion (56) of the balloon matches or nearly matches the outer diameter of the distal portion (12) of the cannula. If the diameter of the distal portion (56) of the balloon meets or exceeds the diameter of the distal portion (12) of the cannula, there will be a smooth and step-free transition from the dilator to the distal portion (12) of the cannula. This transition-free passage of the balloon dilator and cannula construct into a vessel with a small opening greatly eases the placement of the cannula within the vessel. Any damage to the vessel or unnecessary difficulty at the transition between the dilator and the cannula is reduced or eliminated.

Figure 5A:
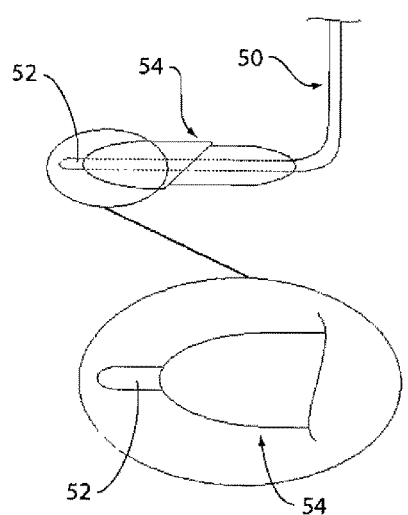
FIG. 5A through E illustrate various tip designs for a balloon dilator.

Referring to FIG. 5A, there is a balloon dilator (50) with balloon (54) and tip (52). The tip (52) is rounded and extends more than one diameter width and distance from the tip of the balloon (54). The intention of the tip (52) is that it will be small enough and long enough to engage the opening made in the heart, vessel, duct, lumen or heart structure for insertion of the balloon dilator, but not so long as that it would easily be caught either on the back wall of the heart or vessel or within another part of the heart or vessel such a nearby branch or Eustachian valve.

Figure 5B:
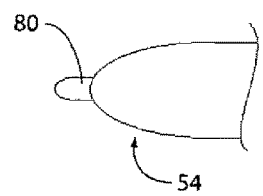

Referring to FIG. 5B with balloon (54) and tip (80), the tip (80) may be shorter than or equal to one diameter width of the tip (80). The length of the tip may vary in length and shape, depending upon a particular application of the balloon dilator.

Figure 5C:
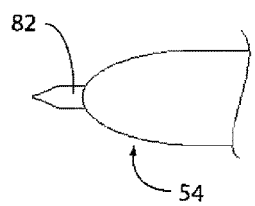

Now referring to FIG. 5C, the balloon (54) of the balloon dilator may have a tip (82) where the tip has a tapered end is slightly rounded or alternatively, may be sharp at the end for a particular application. In one embodiment, the tip may be a needle point.

Figure 5D:
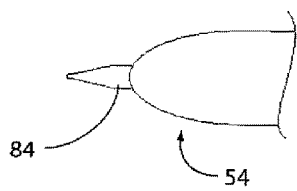

Now referring to FIG. 5D, the balloon (54) may have a tip (84) with an elongated taper to a finer blunt end or sharp end, as required for an application.

Figure 5E:
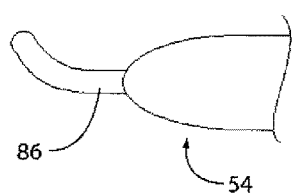

Referring to FIG. 5E, the balloon (54) may have a tip (86) wherein the tip assumes a shape, other than linear, which may include a curve, an angle or multiple curves or angles for particular applications. A curved tip may improve ease of engaging the tip into the opening of a vessel duct lumen or heart structure; in particular, for use in cannulation of the superior or inferior vena cava during heart surgery. As noted previously in the description of FIG. 3, the tip may be hollow and may contain a lumen suitable for passing of a guide wire. A guide wire used in conjunction with a balloon dilator may additionally have straight or curved features such that the dilator is easily placed within the appropriate duct lumen or heart structure and tracks into the appropriate structure such that the balloon dilator may be advanced over the guide wire.

Alternatively, the balloon dilator may have an opening within its shaft suitable for a projection, which serves as the leading tip of the dilator for insertion. This projection itself may have a shape similar to those described in FIG. 5A through 5E, to also accomplish the ease of insertion for the balloon dilator in an atraumatic yet accurate way.

Figure 6A:
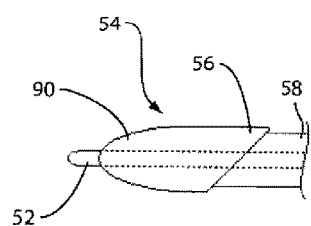
FIG. 6A through F illustrate different taper designs for a balloon dilator.

Now referring to FIG. 6A, balloon (54) of the balloon dilator has a distal portion (56) proximal portion (58) with distal tip (52) and taper (90) of the distal portion of a balloon (56). This taper (90) may have a curvature that is somewhat rounded in nature similar to traditional balloon shapes. This curvature may be altered to improve ease of insertion and minimize transition between the distal tip and the largest diameter of the balloon.

Figure 6B:
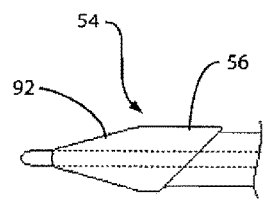

Shown in FIG. 6B is balloon (54) with distal portion of balloon (56) with taper (92). In this embodiment, the taper (92) is a more elongated taper to a sheath, a gentle a gradual transition in diameter between the tip and the maximal portion of the balloon (56). The angle of taper of the balloon may be no more than 45 degrees over any substantial length of the distal portion of the balloon.

Figure 6C:
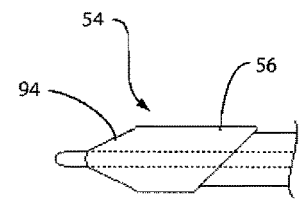

Show in FIG. 6C of balloon (56), the distal portion of (56) and taper (94), has a taper (94), which is somewhat steeper, but still gradual in transition. For some applications, shorter overall distance from the tip of the balloon dilator to its maximal diameter may be required for ease of insertion and minimizing potential for the balloon dilator being hung up or otherwise difficult to insert given the tight space constraints of the operative field.

Figure 6D:
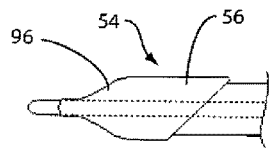

Now referring to FIG. 6D, the distal portion of the balloon (56), the taper (96) wherein the taper (96) may include a gradual change in the dilator of the initial portion of the balloon and then a gentle slow transition up to the maximal diameter of the distal portion of balloon (56).

Figure 6E:
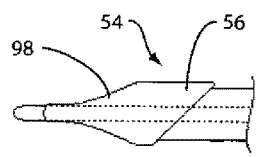

FIG. 6E demonstrates a similar balloon design with even a longer initial distal portion of a balloon (56) or the taper (98) as more than one angle or curvature associated with it.

Figure 6F:
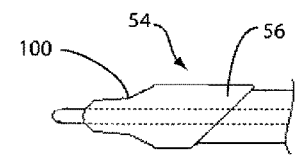

Now referring to FIG. 6F, distal portion (56) of balloon (54) has a taper (100), which includes two different transitions, including a smaller distal portion and then a second taper, which ramps up to the largest diameter of the balloon. The exact taper and transition of the balloon is not meant to be limited by these examples, but demonstrate that for different applications, a variety of transitions of diameter from the distal tip or guide wire to the maximal portion of the balloon may be required for optimal ease of insertion given the exact vessel, duct, lumen or heart structure the balloon dilator's being inserted in and the space constraints of the operator field with that particular application. These tapers may be applied to a balloon with a single largest diameter in addition to balloons with multiple diameters.

Figure 7A:
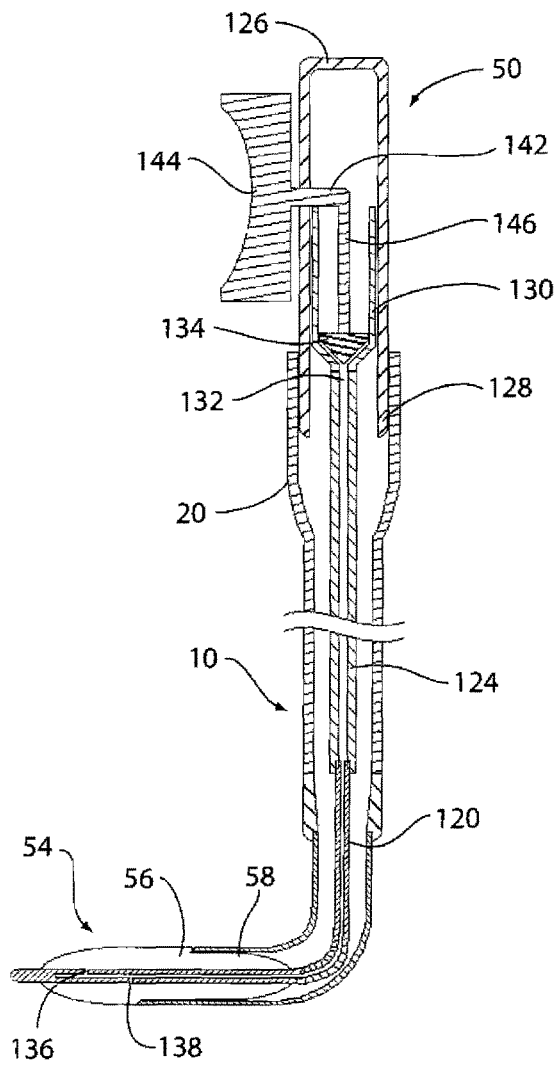
FIG. 7A is a cross-sectional view of a complete balloon dilator, including inflation portion, positioned with a right angle venous cannula where the dilator is in the inflated position.

Shown in FIG. 7A is a cross section of a right-angle-mounted cannula (10) with balloon dilator (50) inserted within it. Balloon dilator (50) includes balloon (54) with distal portion (56) and proximal portion (58). The balloon is inflated by gas or liquid that is delivered to the balloon through channel (132) to the proximal tube (124) of the balloon dilator through the distal tube (120) and out one or more openings (136, 138) into the lumen in the balloon. The proximal portion of the balloon dilator includes housing (126) with distal portion (128), which engages securely with the proximal portion (20) of the right angle venous cannula (10).

Within the proximal portion of the balloon dilator constructor is a syringe-like cylinder (130) and within that, a plunger (134) is connected to shaft (146) and adjacent connecting arm (142) to plunger control handle (144). Plunger (134) in FIG. 7A is shown in the distal most position of cylinder (130) such that the balloon (54) is inflated as shown.

Figure 7B:
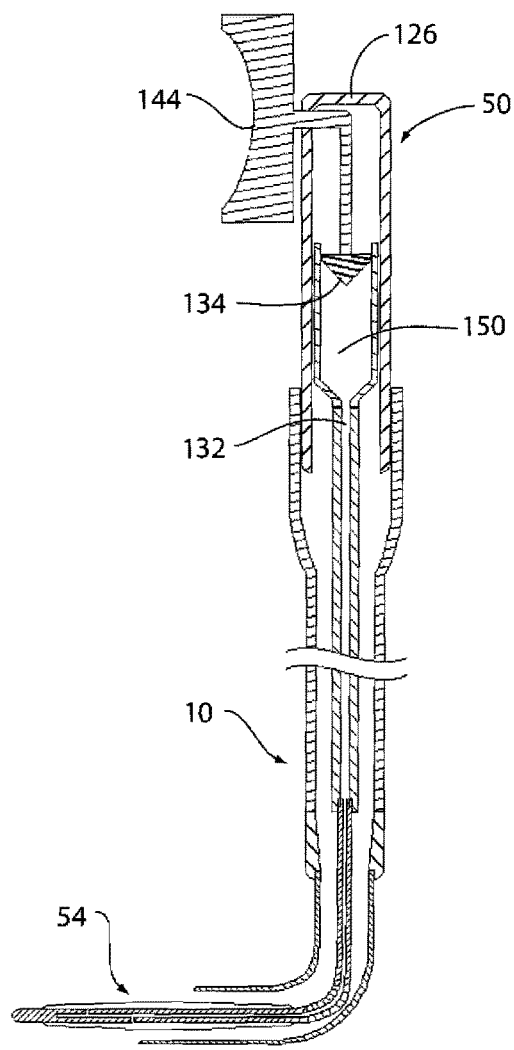
FIG. 7B is a cross-sectional view of a complete balloon dilator positioned with a right angle venous cannula where the balloon is in the deflated position.

Referring now to FIG. 7B, a balloon dilator (50) with balloon (54) and plunger (134) retracted by virtue of moving back the plunger handle (144) such that the plunger tip (134) is in the proximal position. The air or air, gas or liquid has been evacuated out of the balloon (54) and the balloon is now in deflated position as shown. Generally speaking, the balloon would be positioned in an inflated position in a venous or arterial cannula and after insertion into the vessel, duct, lumen or heart structure the balloon would be deflated by retracting back the plunger control handle (144) and the balloon dilator would be removed from the cannula. There may be a locking mechanism that secures the plunger (134) or plunger handle (144) is inserted to a position where the balloon is inflated. This releasable locking mechanism may be unlocked by moving the plunger handle (144) in a direction to unlock the handle prior to retracting the handle. Alternatively a separate locking lever or mechanism may be used in addition to moving the handle (144).

The proximal tube (124) of a balloon dilator (50) may be composed of a material such as a urethane-type plastic, which is rather flexible in nature and relatively small in diameter. Alternatively, it may be composed of a material but not limited to a plastic, metal or alloy wherein the proximal tube (124) has considerable stiffness associated with it. The wire-wound portion of venous cannulas in particular are quite flexible when handling and positioning them within the open chest during cardiac surgery can be difficult given marginal control of the tip of the very flexible cannula. In another embodiment, the proximal tube of the balloon dilator may have a stiffening element adjacent to or around the hollow member delivering fluid to the distal balloon. This may include aluminum or nitinol rod, aluminum tubing or alternatively may include but is not limited to stainless steel, nickel, titanium.

The stiffness of the proximal tube (124) of the balloon dilator (50) may add considerable and desirable stiffness to the balloon dilator venous cannula apparatus; thereby, giving the user much more control of the distal tip of the balloon dilator cannula apparatus during insertion. Additionally, the proximal tube (124) may be malleable such that the tube could be shaped by the surgeon to a particular angle or configuration by manually bending it, and yet still retain adequate stiffness for ease and insertion. There may be a difference in stiffness between one or more portions of the proximal tube (124) whereby a portion may be more flexible than another portion and may be created with a similar or different material.

The increased flexibility may allow ease of transition around the corner of a right-angle venous cannula for improved insertion and removal of the balloon dilator (50) from the venous cannula (10). The balloon (54), distal tube (120) and proximal tube (124) may have lubricious coatings to ease insertion and removal of the balloon dilator from the cannula.

Figure 8:
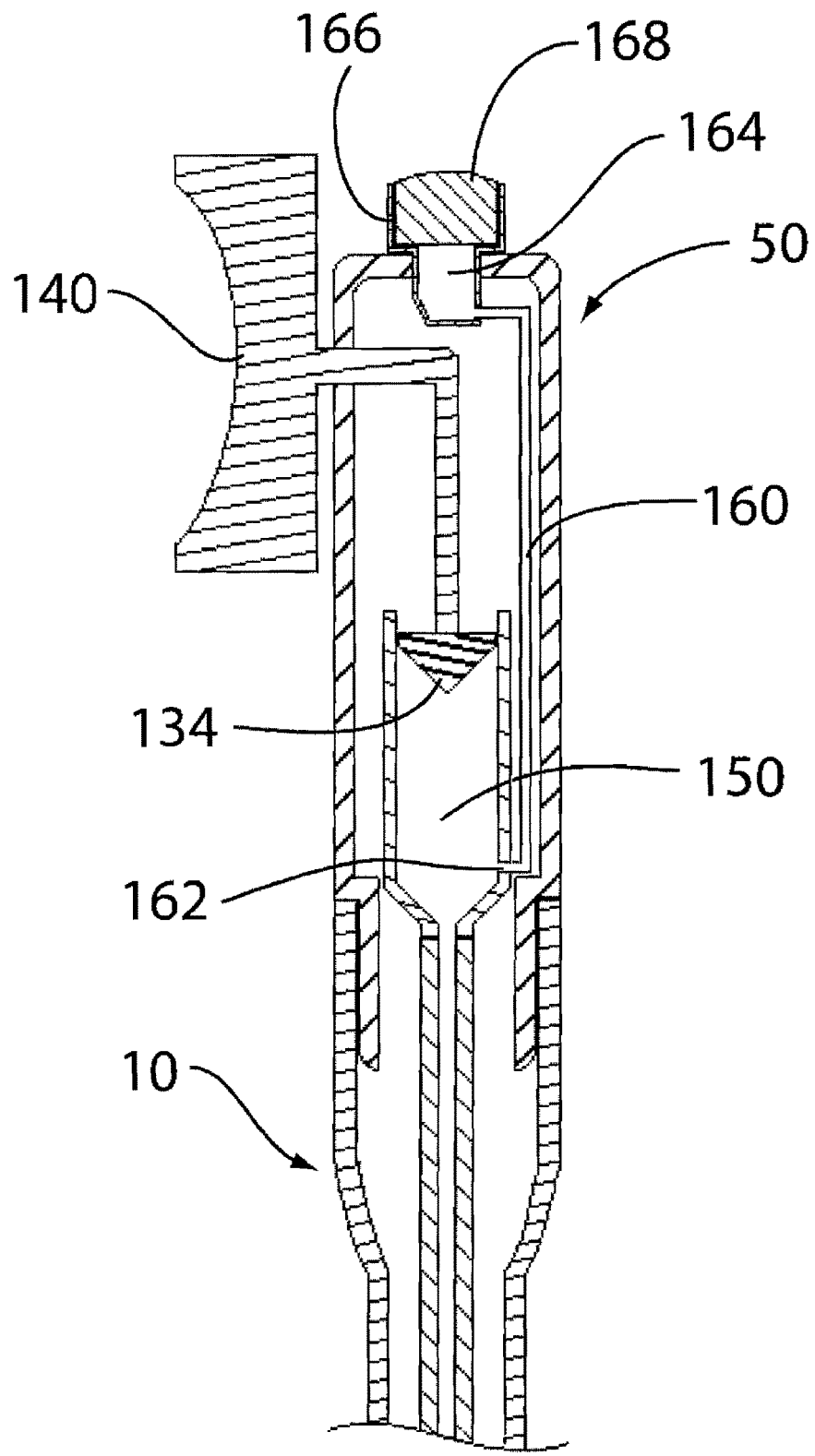
FIG. 8 is a cross-sectional view illustrating the proximal portion of a balloon dilator system.

Referring now to FIG. 8, balloon dilator (50) is positioned within venous cannula (10) with balloon dilator (50) comprising a syringe-like apparatus in this proximal portion, including plunger (134) and syringe chamber space (150). The syringe-like chamber (150) may come prefilled with a gas, liquid or gel for expansion of the balloon prior to insertion. Alternatively, there may be a means by which the user could introduce a gas, gel or liquid for balloon inflation. In another embodiment, there may not be an integrated syringe and the balloon is inflated and deflated by using a separate syringe and an access port on the balloon dilator including but not limited to a needle hub and needless hub or luer connector.

In FIG. 8, the chamber (150) may have an entry hole (162) in communication with a reservoir lumen (160), which leads to a filling reservoir (164) that can be accessed by an external port (166), which may have a penetrable membrane (168). The membrane (168) may be accessible with a needle, such as a blunt needle or may alternatively be a traditional luer fitting. This will allow the user to fill the chamber (150) of the balloon dilator prior to inflation of the balloon.

Figure 9A:
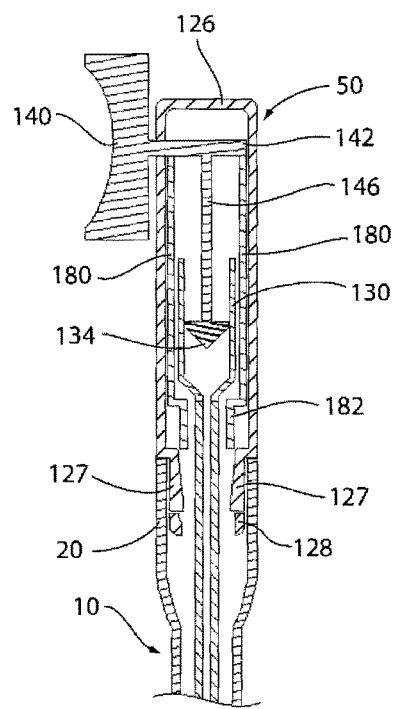
FIG. 9A is a cross-sectional view of the balloon dilator positioned within a right angle venous cannula with a position securement system.

Now referring to FIG. 9A, there is a balloon dilator (50), which is inserted in the proximal portion (20) of venous cannula (10). Balloon dilator (50) has a proximal housing (126), which engages with the distal portion of the venous cannula (20) with two separate elements, a distal element (128) and a mobile element (127). The plunger handle (140) is attached via lumen arm (142) to plunger shaft (146). Lumen arm (142) also attaches to locking cylinder (180) with distal portion (182).

As the handle (140) is advanced distally to inflate the balloon, advancing the plunger (134) into the cylinder (130), the locking cylinder (180) with distal element (182) is advanced to engage with mobile element (127). The shape of the mobile element (127) has an angle or taper such that when the distal portion of a locking cylinder (182) engages with it, then mobile element (127) is forced outward to provide a secure mechanical force to lock the balloon dilator into the proximal portion of the cannula (20). This locking is mechanically coordinated such that when the balloon is inflated for insertion, the mobile element (127) is pushed outward into the cannula to ensure secure position of the balloon dilator within the cannula.

As the handle (140) is retracted to deflate the balloon, the distal portion of the locking cylinder (182) disengages and mobile element (127) and the locking force applied proximally to the venous cannula (20) is removed. The balloon dilator (50) can then be smoothly removed from the cannula without difficulty. Due to the delicate structures these cannulas are often placed in, it is necessary that the removal of the dilator from the cannula be smooth, quickly and without difficulty or many additional movements.

The simultaneous locking of the balloon dilator within the cannula during balloon inflation and unlocking at the time of balloon deflation occurs assures that the balloon dilator is securely positioned when needed, but then free to be easily removed once the balloon is deflated with the intent of balloon dilator removal.

Figure 9B:
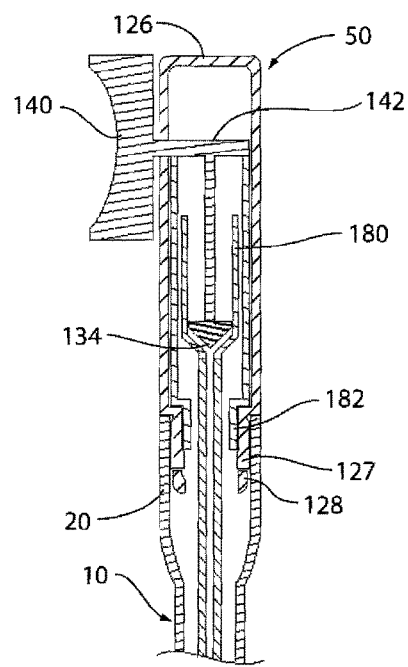
FIG. 9B is a cross-sectional view of a balloon dilator system positioned within a venous cannula wherein the securement system of the balloon dilator has been activated.
Figure 9C:
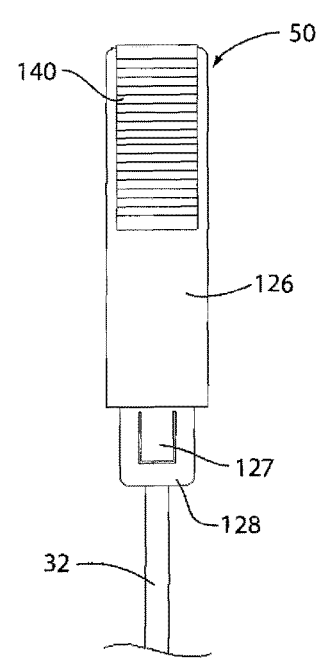
FIG. 9C is a lateral view of the proximal end of the balloon dilator system with the cannula position securement means.

Referring to FIG. 9C, this is an external view of the balloon dilator (50) with plunger handle (140), proximal portion of housing (126), which demonstrates one configuration of the mobile element (127) adjacent to distal element 128, which engages with the venous cannula. There are an array of mobile element designs (127) that could be utilized with this to provide one or more points of engagement within the venous cannula for securement. In this design, there are two opposite mobile elements (127), but one or more may be used for securement.

Figure 10A:
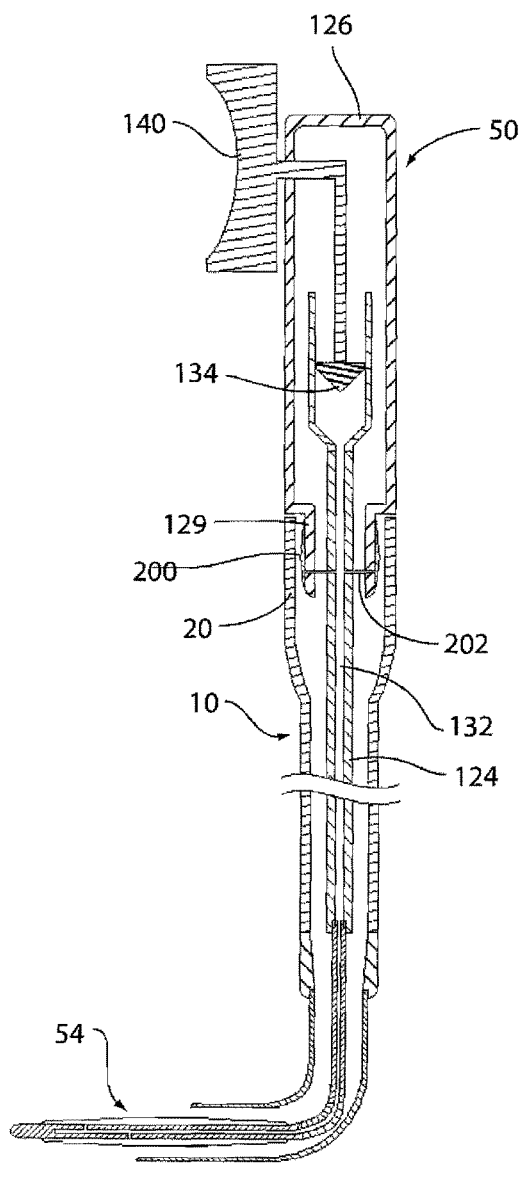
FIG. 10A is a cross-sectional view of a balloon dilator system, positioned within a right angle venous cannula with a proximal dilator position securement system using a balloon which is in the deflated position.

Now referring to FIG. 10A, there is balloon dilator (50) with distal balloon (54), which includes plunger handle (140) and plunger (134) with channel (132) of the proximal tube (124), which delivers the gas or the liquid to the distal balloon (54). Another embodiment of the securement system of the balloon dilator (50) to the proximal portion of the cannula (20) may include a proximal balloon (200) around the distal portion (129) of the housing (126) of balloon dilator such that the proximal balloon (200) may be inflated concurrently with the distal balloon (54).

As shown in FIG. 10A, the distal balloon (54) and proximal balloon (200) are in the deflated position and the plunger (134) is in the retracted position.

Figure 10B:
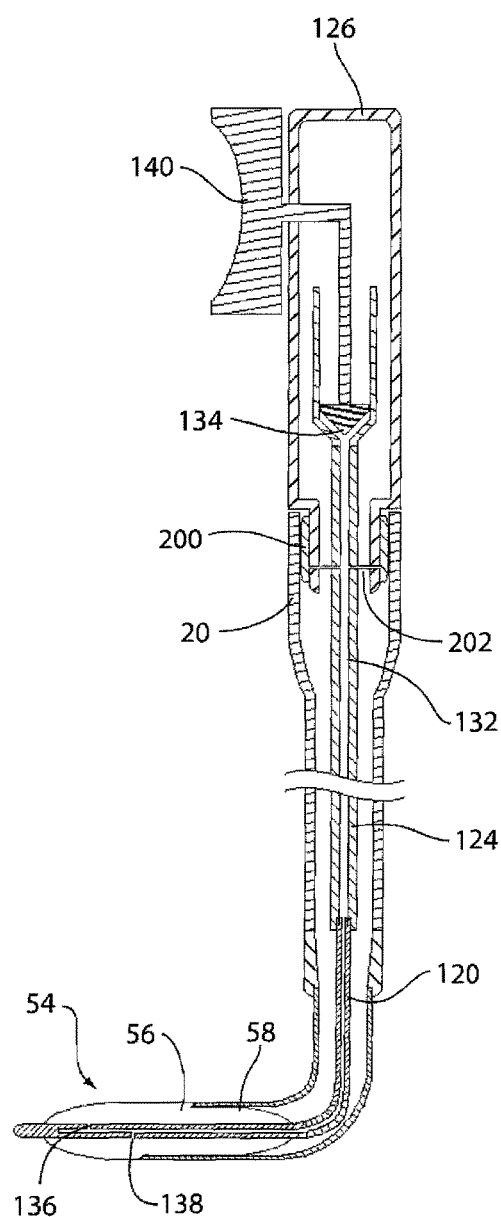
FIG. 10B is a cross-sectional view of a balloon dilator system positioned within a right angle venous cannula wherein the balloon dilator system has a proximal dilator position securement balloon which is in the inflated position.

Shown in FIG. 10B, the plunger (134) has been advanced to the distal most position and air, gas, gel or other inflation fluid is delivered via channel (132) to distal balloon (54) through openings (136) and (138). The inflation fluid is also delivered via openings (202) into proximal balloon (200) for concurrent inflation. The proximal balloon (200) and distal balloon (54) may both be inflated just prior to the time that the balloon dilator and cannula apparatus is handed to the surgeon for insertion.

After insertion of the cannula, the vessel, duct, lumen or heart structure handle (140) of the balloon dilator (50) would be retracted to the proximal position; thereby, evacuating the fluid from the distal balloon (54) and the proximal balloon (200), thereby releasing the locking or securement force between the balloon dilator and proximal portion of the venous cannula for ease of removal of the balloon dilator from the venous cannula.

The proximal balloon (200), proximal tube (124), distal tube (120), including distal balloon (54) may all have lubricious coating such that the balloon dilator may be easily removed from the venous cannula (10) without disrupting or moving the position of the venous cannula.

There is a need for quick and easy removal of the balloon dilator after insertion of the cannula. In another embodiment, there may be no considerable attachment between the balloon dilator and the proximal aspect of the cannula. The inflation of a portion of the balloon dilator within the distal aspect of the cannula may provide adequate securement of the balloon dilator position relative to the position of the cannula. After insertion of the cannula, the balloon may be deflated with removal of the balloon dilator. There may be a visual or mechanical marking system that denotes the desired relative position of the balloon dilator and the proximal portion of the cannula. In another embodiment, there may be a projection from the balloon dilator such as a disk, rod or other shape that provides an indicator or stop to how far the balloon dilator should be inserted into the cannula. This may both ease positioning of the balloon dilator within the cannula and prohibit inadvertent over insertion of the balloon too far past the distal tip of the cannula. In another embodiment, the stiffening element of the balloon dilator may be contiguous with or attached to the positioning projection that indicates the desired position of the balloon dilator relative to the proximal tip of the cannula.

Figure 11A:
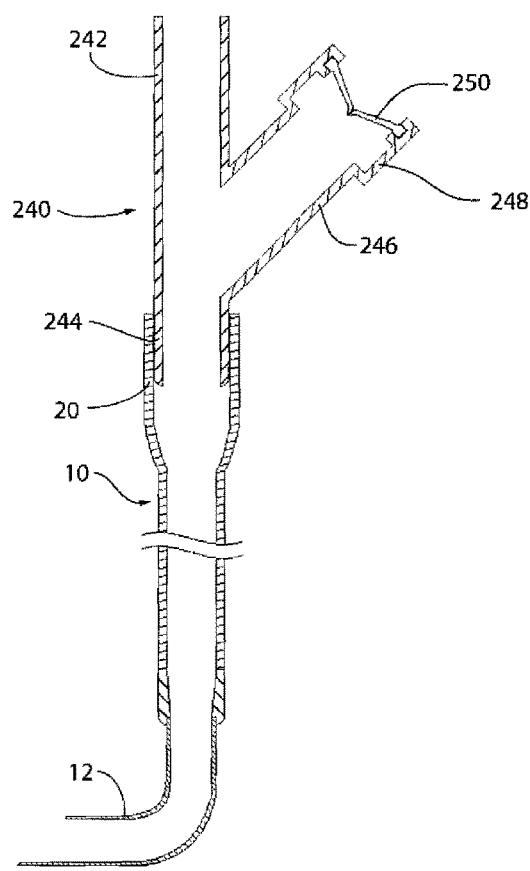
FIG. 11A is a cross-sectional view of a cannula with a Y connector inserted into the proximal aspect of the cannula with a valve for a balloon dilator cannula.

Now referring to FIG. 11A, what is depicted is a cross-sectional view of a bifurcated connector (240) with distal portion (244), which engages securely with the proximal portion (20) of cannula (10). Bifurcated connector (240) has a proximal port (242), which may be in line with distal connector portion (244) and cannula (10), additionally, there is secondary proximal port (246) which comes off at an angle relative to axis of the distal portion 244 and includes proximal housing (248) and valve (250). This bifurcated proximal connector (240) allows the option of insertion of a balloon dilator into a cannula where the cannula can be connected to tubing that leads to the cardiopulmonary bypass or ECMO circuit prior to the cannula being inserted in the patient.

The proximal port (242) may be connected to tubing of the mechanical circulatory support circuit and allow the balloon dilator to then be put through the valve (250) of the additional proximal portion (246).

Figure 11B:
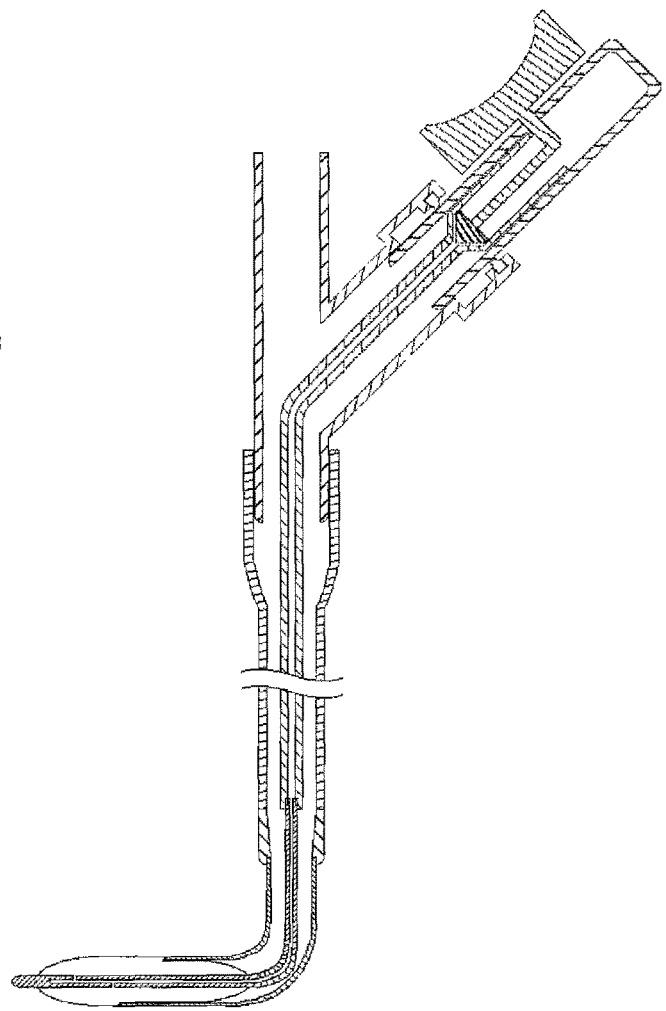
FIG. 11B is a cross-sectional view of a cannula with a Y connector and a balloon dilator inserted through a valve in one arm of the Y connector.

Shown in FIG. 11B is balloon dilator (50) with proximal tube (124), housing (126) with distal portion (128) of the housing, which is engaged through the valve (250), proximal housing (248), and secondary proximal port (246) of the bifurcated connector (240). In this embodiment, the venous cannula could be pre-connected to the cardiopulmonary bypass or other circuit via proximal inline connector, portion (242) where balloon dilator (50) can be removed from the cannula after the cannula is inserted in the patient and the mechanical circulatory support could immediately commence. The balloon dilator used with the bifurcated proximal connector may utilize a means to reversibly secure it in position with securement means such as those shown in FIGS. 9 and 10. After the balloon dilator is removed from the valve (250), a plug may be inserted through the valve that extends into the secondary proximal port (246) and may end at or near the take off of the other proximal port (242). This plug may prevent the entrainment of air through the valve (250) while the cannula is used for cardiopulmonary bypass or ECMO, especially if vacuum is used.

Figure 12A:
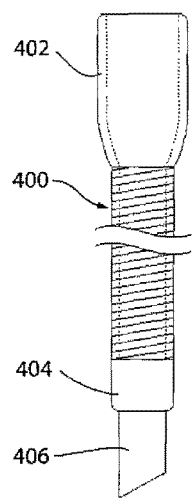
FIG. 12A is a lateral view of an arterial cannula.

Referring now to FIG. 12A. There is a straight cannula (400) with a proximal portion (402), connector (404), and distal portion (406). This may represent a standard aortic cannula that may be used in cardiopulmonary bypass or other straight cannula used for peripheral access for cardiopulmonary bypass or ECMO. This, and like designs, may be used for cannulation of the aorta or another artery, vessel, duct, lumen or cardiac structure for institution of cardiopulmonary bypass or ECMO support or any other need for luminal access.

Figure 12B:
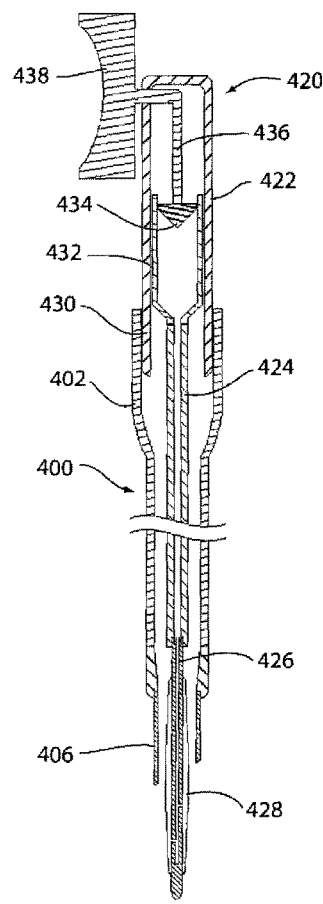
FIG. 12B is a cross-sectional view of a balloon dilator system positioned within an arterial cannula where the balloon is in a deflated position.

Referring now to FIG. 12B, there is a balloon dilator (420) positioned within the cannula (400), balloon dilator having a proximal portion of (422) with an engagement portion (430), which secures the balloon dilator to the proximal portion of the cannula (402). In this configuration, the balloon (428) is in the deflated position and correspondingly the plunger (434) and handle (438) are in the retracted position.

Figure 12C:
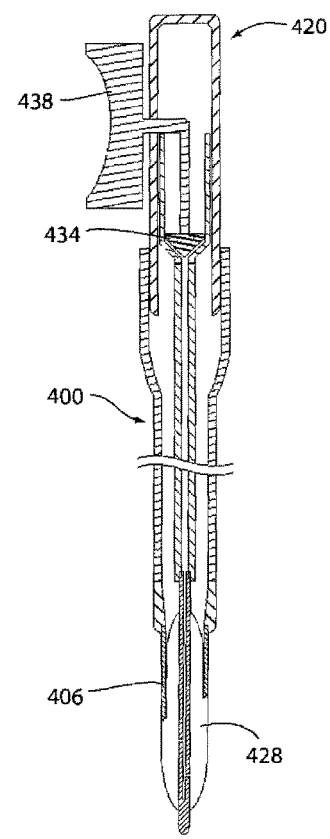
FIG. 12C is a balloon dilator system positioned within an arterial cannula wherein the balloon is inflated.

Referring now to FIG. 12C, the balloon dilator (420) now has an inflated balloon (428), and correspondingly the plunger (434) and handle (438) are in distal advanced position. In this embodiment the balloon (428), also has a distal portion, which is the same, similar, or larger diameter as the outer diameter of the distal portion (406) of the cannula to provide a smooth transition between the balloon dilator and the aortic cannula.

Insertion of a cannula with a balloon dilator such as that shown in above Figures may begin with placement of a balloon dilator within the cannula such that a portion of the balloon protrudes past the distal tip of the cannula. The balloon of the balloon dilator may then be inflated to provide a tapered insertion for the distal aspect of the cannula and also releasable secure the balloon dilator to the cannula. Additional securement of the balloon dilator to the cannula may be used as shown in FIGS. 8-12. With the balloon dilator in place, the cannula and dilator are advanced into a hole or otherwise opening in the vessel duct, lumen or heart structure. Once the tip of the cannula is in the desired place within the vessel, the balloon is deflated. Additional securement features may also be deflated or disengaged at the same time as or independent of balloon deflation. The balloon dilator is then removed and the cannula is secured by typical means such as a purse string cinched with a tourniquet followed by placing a tie around the cannula and tourniquet. Following the use of the cannula, the cannula may simply be removed in standard fashion without the balloon dilator.

Figure 13:
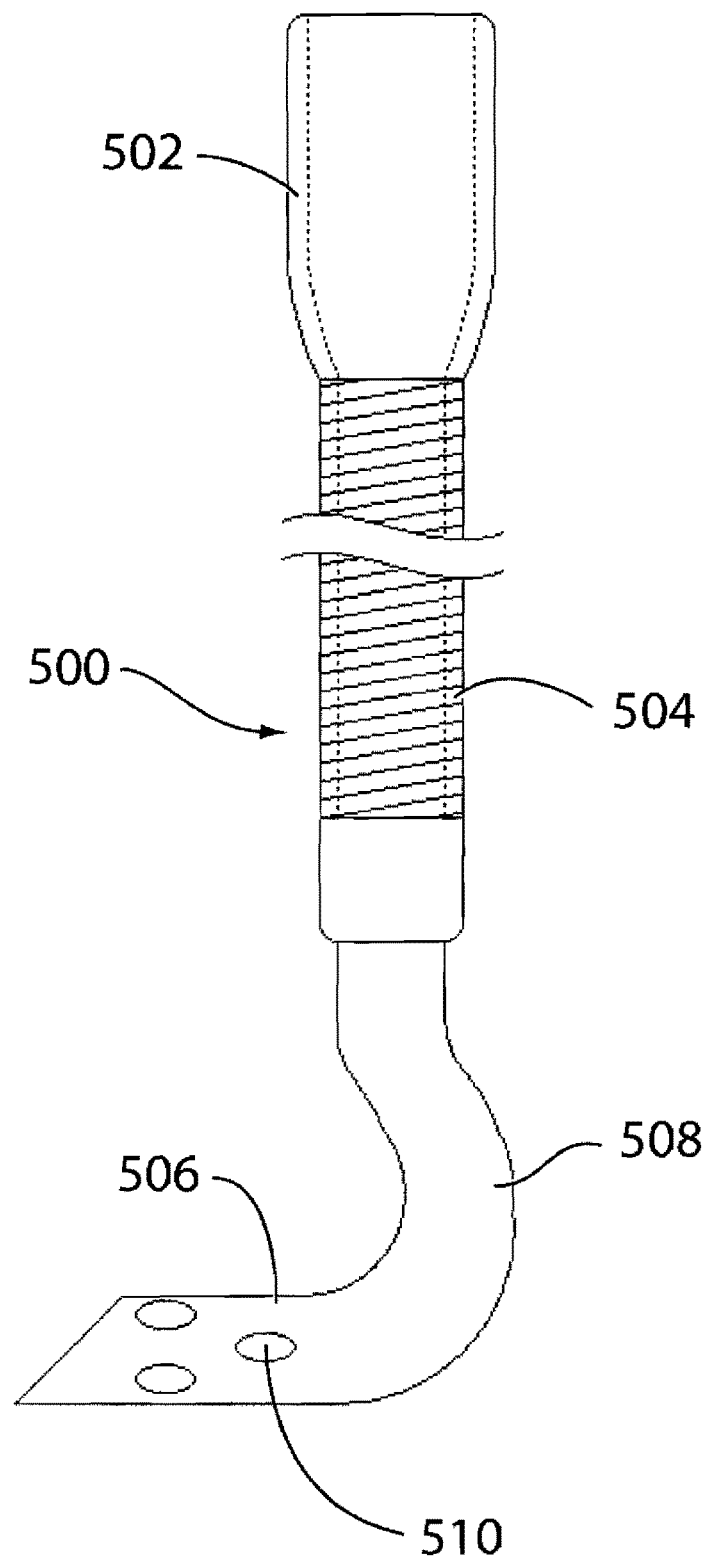
FIG. 13 is a lateral view of a right angle venous cannula with a metal tip portion of defined curvature.

Referring now to FIG. 13, there is a venous cannula (500) with proximal portion (502) a wire wound, kink resistant tubing portion (504), and a distal portion (506), which includes a curve with curvature (508) with one or more radii and direction of curvature including side holes (510) in the distal portion (506). This cannula may have a C shape or similar shape.

The curvature of a typical right-angle venous cannula may be modified to include a larger diameter radius or more than one radii of curvature to both accommodate a smooth transition of a balloon dilator into and out of the venous cannula, as well as to improve the flow characteristic of the blood within the cannula. Improving the inflow characteristics may minimize the pressure drop across the cannula and improve venous return.

Figure 14A:
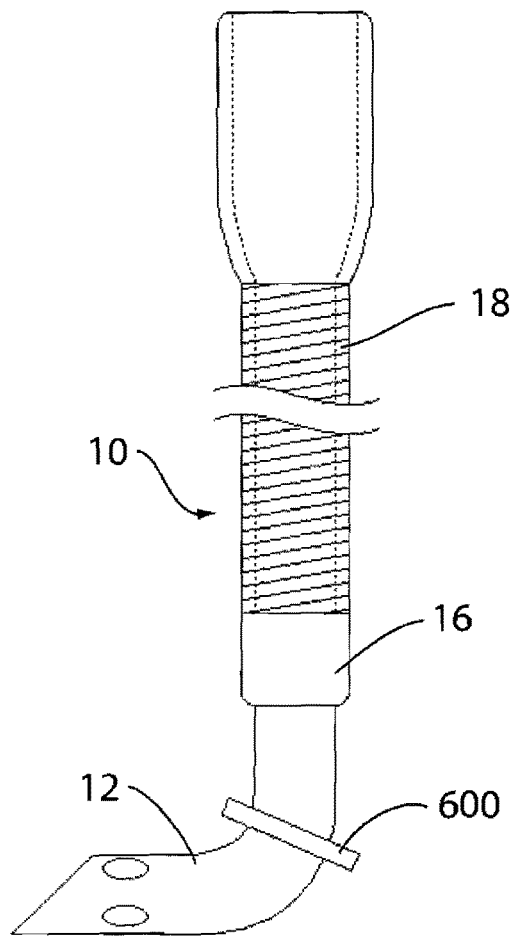
FIG. 14A is a lateral view of a right angle venous cannula with a depth positioner.

Now, referring to FIG. 14A, there is a venous cannula (10) with wire-wound portion (18), connected portion (16) and distal end (12) with a depth stop (600) positioned on the distal portion (12). This depth stop may be fixed or adjustable. It may be comprised of the same material as the distal tip of the cannula or it may be a separate material.

This distal tip could be a rubber flange that is tightly fitting and applied by the user just prior to insertion of cannula, or it could be a full circumferential or partial circumferential feature that provides a depth stop for the cannula. This reduces the chance that the cannula would be put in so far as to curve up into one aspect of the wall of the vessel and have decreased venous return. This feature coupled with a balloon dilator would facilitate smooth and exact insertion of a cannula and provide visual feedback to the user that the cannula remained in the desired position after the balloon dilator was removed.

Figure 14B:
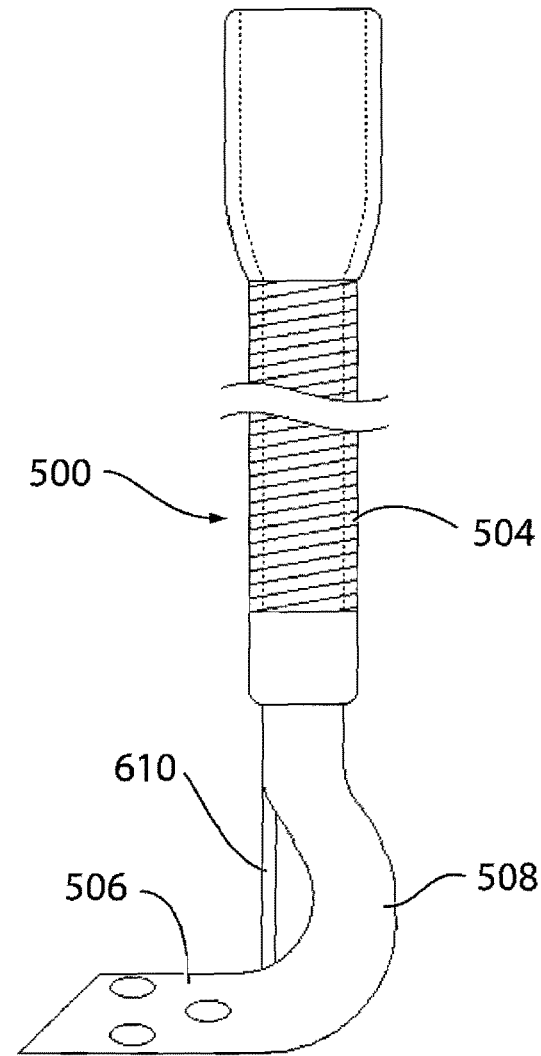
FIG. 14B is a right angle venous cannula with a depth-limiting feature.

Another embodiment shown in FIG. 14B has a venous cannula (500) with distal portion (506) including a curvature (508) with a depth-stop feature (610), which may extend from one portion of the distal tip (506) to another. This feature would prevent over insertion of the cannula even with a larger radius of curvature of the cannula than the surgeon may be accustomed to with the current design.

Depth-stop feature would again ensure accurate position of the cannula minimizing the chances the cannula would be tipped or angled in a direction to position against a wall or into a branch vessel and impede venous return in any way.

INCORPORATION BY REFERENCE

All patents, published patent applications and other references disclosed herein are hereby expressly incorporated in their entirety by reference. It should be understood that the forgoing disclosure and description of the present invention are illustrated and explanatory thereof and various changes in the size, shape, and material composition, as well as in the description of the embodiments, may be made without departure from the spirit of the invention as defined by the appended claims.

What is claimed is:

1. A cannula kit, comprising:
   a) a cannula with a distal portion arranged to engage a vessel, duct, lumen or cardiac structure;
   b) a balloon dilator structure with a proximal portion and a distal portion, wherein the distal portion of the balloon dilator structure is arranged to extend beyond the distal portion of the cannula; and
   c) wherein the distal portion of the balloon dilator structure has a balloon element that is inflated and deflated, wherein the balloon element has at least two diameters when inflated such that a distal portion of the balloon element is outside of the cannula, a proximal portion of the balloon element is within the cannula, a maximal diameter of the distal portion of the balloon element is larger than a maximal diameter of the proximal portion of the balloon element, and further wherein a transition between said maximal diameters of said distal portion and said proximal portion of the balloon element is angled, and still further wherein the maximal diameter of said distal portion of the balloon element is slightly smaller than, equal to, or slightly larger than an outside diameter of the distal portion of the cannula.

2. The cannula kit according to claim 1, wherein the balloon dilator structure further comprises a tube, and has a stiffness along the tube that exceeds a stiffness of the cannula.

3. The cannula kit according to claim 2, wherein the tube is malleable.

4. The cannula kit according to claim 3, wherein the balloon dilator structure is bent or shaped in an area of the tube.

5. The cannula kit according to claim 1, wherein the cannula and the balloon dilator structure each are bent at at least one angle along their length that exceeds 45°.

6. The cannula kit according to claim 1, wherein a transition from a distal tip of the balloon element to said maximal diameter of said distal portion of the balloon element has at least one taper angle.

7. The cannula kit according to claim 1, wherein a transition from a distal tip of the balloon element to said maximal diameter of said distal portion of the balloon element has a taper that is concave.

8. The cannula kit according to claim 1, wherein the proximal portion of said balloon dilator structure has a port, luer connector or opening for attachment of a syringe for balloon inflation or deflation.

9. The cannula kit according to claim 1, wherein the proximal portion of said balloon dilator structure has an integrated syringe for inflation and deflation of the balloon element.

10. The cannula kit according to claim 1, wherein the proximal portion of said balloon dilator structure interfaces with the cannula, and a radial force is releasably applied to an internal diameter of the cannula to secure the balloon dilator structure to the cannula.

11. The cannula kit according to claim 10, wherein said balloon dilator structure further comprises a housing, and further wherein the radial force is applied to the cannula by a second balloon positioned around a distal portion of the housing in an area where the balloon dilator structure interfaces with a proximal portion of the cannula.

12. The cannula kit according to claim 11, wherein the second balloon positioned around the distal portion of the housing and the balloon element at the distal portion of the balloon dilator structure are inflated and deflated by a common syringe.

13. The cannula kit according to claim 1, wherein the cannula has two proximal openings, wherein one opening of the two proximal openings has a valve where the balloon dilator structure is positioned through the valve and extend beyond the distal portion of the cannula.

14. The cannula kit according to claim 1, wherein the distal portion of the cannula has a portion that is larger in diameter than a distal tip of the cannula to limit a depth of insertion of the cannula.

15. The cannula kit of claim 1, further comprising:
   d) a means for inflating and deflating said balloon element, such that in an inflated condition, said balloon element has a largest diameter that matches or nearly matches the outside diameter of said distal portion of said cannula, and
   e) a means for releasably securing said balloon dilator structure to said cannula for ease of withdrawing said balloon dilator structure out of a proximal portion of said cannula.

16. The cannula kit of claim 15, further comprising a means for positioning said balloon element at least in its deflated state such that said proximal portion of said balloon element is located within said cannula, and said distal portion of said balloon element extends distally out of said distal portion of said cannula.

17. The cannula kit of claim 15, wherein said cannula is a right-angle cannula.

18. The cannula kit of claim 15, wherein in said inflated condition, said balloon element comprises multiple diameters.

19. The cannula kit of claim 18, wherein the proximal portion of said balloon element has a diameter equal to an inside diameter of said distal portion of said cannula.

20. The cannula kit of claim 15, wherein said balloon dilator structure further comprises a distal tip mounted to said distal portion of said balloon element to facilitate entry into an undilated vessel, duct, lumen or cardiac structure.

21. The cannula kit of claim 15, wherein said means for inflating and deflating said balloon element comprises (i) a cylinder, (ii) a plunger, (iii) a housing for said cylinder and plunger, and (iv) a handle external to said housing and connected to said plunger, said balloon element being in fluid communication with said cylinder, whereby moving said handle moves said plunger along a longitudinal axis within said cylinder, thereby inflating or deflating said balloon element.

22. The cannula kit according to claim 15, wherein, in said inflated condition, said distal portion of said dilation balloon provides a smooth transition between said balloon dilator structure and an outer wall of said cannula.

23. The cannula kit of claim 1, wherein the balloon dilator structure further comprises a stiffening element.

24. A cannula kit, comprising:
   a) a cannula with a distal portion arranged to engage a vessel, duct, lumen or cardiac structure;
   b) a balloon dilator structure with a proximal portion and a distal portion, wherein the distal portion of the balloon dilator structure is arranged to extend beyond the distal portion of the cannula; and
   c) wherein the distal portion of the balloon dilator structure has a balloon element that is inflated and deflated, wherein the balloon element has at least two diameters when inflated such that a distal portion of the balloon element is outside of the cannula, a proximal portion of the balloon element is within the cannula, a diameter of the proximal portion of the balloon element is equal to an internal diameter of the distal portion of the cannula, and a maximal diameter of the balloon element is slightly smaller than, equal to, or slightly larger than an outside diameter of the distal portion of the cannula; and
   d) wherein said cannula kit does not require a guidewire for said cannula to engage the vessel, duct, lumen, or cardiac structure.

25. The cannula kit of claim 24, wherein said distal portion of said cannula is cut at a 45 degree angle to facilitate entry into the vessel, duct, lumen or cardiac structure.

26. The cannula kit of claim 24, wherein said distal portion of said cannula is cut at an angle.

27. A cannula kit, comprising:
   a) a cannula with a distal portion arranged to engage a vessel, duct, lumen or cardiac structure;
   b) a balloon dilator structure with a proximal portion and a distal portion, wherein the distal portion of the balloon dilator structure is arranged to extend beyond the distal portion of the cannula; and
   c) wherein the distal portion of the balloon dilator structure has a balloon element that is inflated and deflated, wherein the balloon element has at least two diameters when inflated such that a distal portion of the balloon element is outside of the cannula, a proximal portion of the balloon element is within the cannula, a diameter of the proximal portion of the balloon element is equal to an internal diameter of the distal portion of the cannula, and a maximal diameter of the balloon element is slightly smaller than, equal to, or slightly larger than an outside diameter of the distal portion of the cannula; and
   wherein said distal portion of said cannula is cut at a 45 degree angle.

28. The cannula kit of claim 1, wherein said maximal diameter of said proximal portion of the balloon element is equal to an inside diameter of said distal portion of said cannula.

\* \* \* \* \*